United States Patent [19]

Fullington et al.

[11] 4,138,559

[45] Feb. 6, 1979

[54] RECOVERY OF CHLORINE AND CYANURIC ACID VALUES FROM POLYCHLOROISOCYANURIC ACIDS AND SALTS THEREOF

[75] Inventors: Michael C. Fullington; Louis C. Hirdler, both of Lake Charles, La.

[73] Assignee: Olin Corporation, New Haven, Conn.

[21] Appl. No.: 873,462

[22] Filed: Jan. 30, 1978

[51] Int. Cl.$^2$ .................. C07D 251/32; C01B 7/07
[52] U.S. Cl. .................. 544/192; 544/190; 423/500; 423/504
[58] Field of Search ............... 544/190, 192; 423/500, 423/504

[56] References Cited

U.S. PATENT DOCUMENTS

| 3,835,136 | 9/1974 | Hirdler et al. | 544/192 |
| 3,846,424 | 11/1974 | Hirdler et al. | 544/192 |
| 3,944,548 | 3/1976 | Manganaro et al. | 544/192 |
| 4,003,899 | 1/1977 | Manganaro et al. | 544/192 |

OTHER PUBLICATIONS

Brooks., *Chemical Engineering*, 18 Feb. 1974, p. 152.

*Primary Examiner*—John M. Ford
*Attorney, Agent, or Firm*—James B. Haglind; Donald F. Clements

[57] ABSTRACT

A process for recovering chlorine values from an aqueous solution of a chloroisocyanuric acid compound is disclosed. After reacting a mineral acid with the aqueous solution to form an acidified reaction mixture containing dissolved chlorine, the reaction mixture is fed to a stripping column which employs an inert gas to remove the dissolved chlorine. The stripping column is maintained to provide a continuous liquid phase and a non-continuous gas phase. Chlorine gas is readily recovered in a vessel such as a scrubber. Cyanuric acid may be subsequently recovered from the chlorine-depleted solution.

22 Claims, 1 Drawing Figure

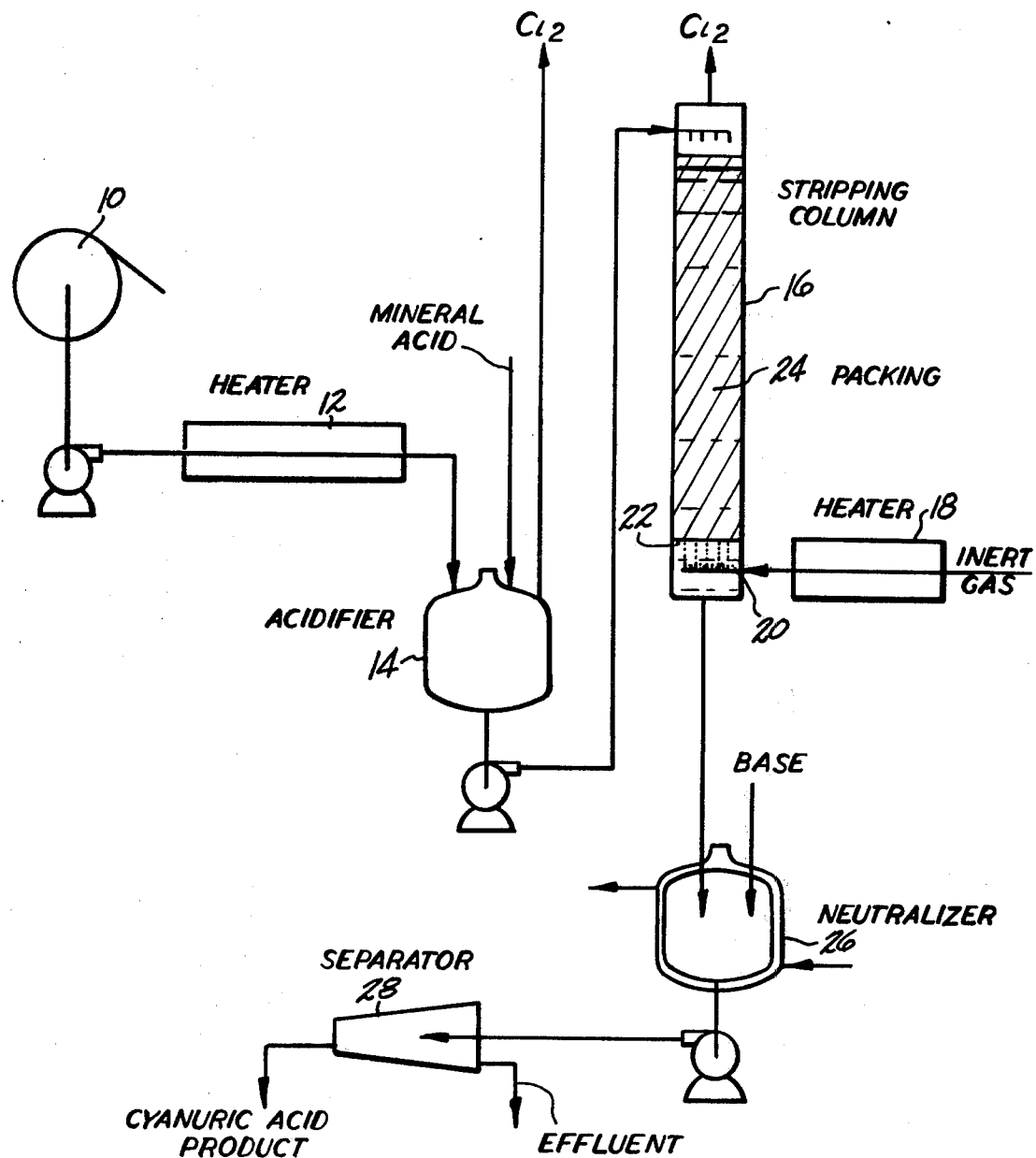

RECOVERY OF CHLORINE AND CYANURIC ACID VALUES FROM POLYCHLOROISOCYANURIC ACIDS AND SALTS THEREOF

This invention relates to the recovery of chlorine and cyanuric acid values from aqueous solutions of chlorinated s-triazine compounds selected from the group consisting of polychloroisocyanuric acids, alkali metal salts and mixtures thereof.

In the production of polychloroisocyanuric acids such as dichloroisocyanuric acid and trichloroisocyanuric acid, following product recovery, solutions containing varying amounts of product remain to be disposed of. In addition to containing economically valuable materials, the solutions pose a pollution problem if, for example, they are added to public waterways such as rivers and streams.

Chlorine and cyanuric acid values have previously been recovered by reacting the aqueous solutions of chlorinated s-triazine compounds with mineral acids such as hydrochloric acid or sulfuric acid in a vessel such as a packed column. The reaction produces an aqueous solution containing dissolved chlorine and cyanuric acid. Chlorine is stripped from the solution by passing an inert gas through the solution. It is important to effectively and efficiently recover the chlorine gas without substantial amounts of cyanuric acid being deposited as a scale on reactor surfaces, column packing and other equipment used in chlorine recovery. It is this aspect of the recovery process which has been ignored in processes of the prior art.

An object of the present invention is to provide a process for the recovery of valuable materials from aqueous solutions obtained in the production of polychloroisocyanuric acids and alkali metal salts thereof.

Another object of the present invention is to provide a process having improved recovery of chlorine and cyanuric acid compounds from aqueous solutions of polychloroisocyanuric acids and alkali metal salts thereof.

A further object of the process of the present invention is to provide a process in which the disposal of waste solutions poses no pollution problem.

A still further object of the present invention is to provide a process which minimizes the cost of equipment such as stripping columns and gas scrubbers.

An additional object of the present invention is to provide a stripping process having reduced requirements for acids and inert gases used.

Yet another object of the present invention is to provide a process which prevents fouling of reactor surfaces and recovery components.

These and other objects of the invention are accomplished in a process for recovering chlorine values from an aqueous solution of a chloroisocyanuric acid compound selected from the group consisting of polychloroisocyanuric acids, alkali metal salts of polychloroisocyanuric acids and mixtures thereof. A mineral acid is reacted with the aqueous solution of the chloroisocyanuric acid compound to produce a reaction mixture containing dissolved chlorine and cyanuric acid in an aqueous solution. The aqueous solution is fed to a stripping column and the chlorine is removed from the reaction mixture with an inert gas. The process improvement comprises maintaining a continuous liquid phase and a non-continuous gas phase in the stripping column.

The accompanying FIGURE represents a flow diagram of the improved process of the present invention.

In operating the process illustrated in the FIGURE, an aqueous solution containing a polychloroisocyanuric acid or salt thereof is obtained, for example, as a filtrate from filter 10 and is pumped to heater 12. As the aqueous solution passes through heater 12, it is heated and fed to reactor 14. Simultaneously fed to reactor 14 is a mineral acid to form an acidified aqueous solution containing dissolved chlorine, an alkali metal chloride, hypochlorous acid and cyanuric acid. During acidification, a portion of the chlorine may be evolved and can be removed from the upper end of the reactor 14. The acidified aqueous solution is pumped to the upper end of stripping column 16. A gas which is inert to the reaction conditions is heated in heater 18 and fed to the lower end of stripping column 16 through gas inlet 20 to flow countercurrently through the acidified aqueous solution. The stripping reaction is conducted with the level of acidified aqueous solution above support plate 22 and packing material 24 is partially or completely submerged by the acidified aqueous solution. A gaseous mixture containing substantially all of the chlorine evolved from the chloroisocyanuric acid compound is removed from the upper part of stripping column 16. The chlorine depleted acidified aqueous solution is fed to neutralizer reactor 26 where it is treated with an alkali metal base. Following neutralization, the aqueous solution is pumped to separator 28 where the resulting cyanuric acid product is separated from the effluent solution.

More in detail, one of the reactants in the process of this invention is an aqueous solution of a chloroisocyanuric acid compound such as those obtained from the production of dichloroisocyanuric acid, trichloroisocyanuric acid and alkali metal salts thereof. The salts can be, for example, alkali metal chloroisocyanurates, such as potassium and sodium dichloroisocyanurate. While the aqueous solution treated by the process of this invention can contain any proportion of chloroisocyanuric acid compound, the aqueous solution generally contains from about 0.01 to about 30 and frequently from about 0.1 to about 5 percent by weight of the chloroisocyanurate. Often the aqueous solution also contains an alkali metal chloride such as sodium chloride. Depending upon the source of the solution, the amount of alkali metal chloride can vary widely, and can constitute, for example, from about 0 to about 25 percent by weight and preferably from about 4 to about 15 percent by weight of the aqueous solution. High concentrations (up to about 30 percent by weight) of chloroisocyanuric acid compound are present in aqueous solutions containing, for example, an alkali metal polychloroisocyanurate such as sodium dichloroisocyanurate. When the alkali metal polychloroisocyanurate is present in high concentrations, usually the solution contains little or no alkali metal chloride. Aqueous solutions containing chloroisocyanuric acid compounds such as dichloro- and trichloroisocyanuric acid usually have concentrations of from about 0.01 to about 3 percent by weight. These solutions, however, frequently contain high concentrations of alkali metal chloride. In addition, the aqueous solution may contain trace amounts of cyanuric acid and other compounds which are often present as minor impurities. The balance of the solution is generally water, which ranges, for example, from about 70 to about 95, and preferably from about 75 to about 95 percent by weight of the aqueous solution.

Aqueous solutions suitable for use in the process of the present invention include those by-product solutions obtained in the production of dichloroisocyanuric acid and/or trichloroisocyanuric acid. For example, in one type of process, cyanuric acid is reacted with sodium hydroxide to form disodium cyanurate or trisodium cyanurate, which is then chlorinated by the addition of chlorine gas to produce a slurry containing di- or trichloroisocyanuric acid. The slurry is filtered to recover the desired product, and a by-product solution containing varying concentrations of the di- or trichloroisocyanuric acid remains. U.S. Pat. Nos. 2,956,056; 2,964,525; 2,969,360; 2,975,178; 3,073,083; 3,178,429; 3,189,609; and 3,534,033 exemplify this technique for producing solutions suitable for use in the process of the present invention. Other suitable techniques for producing by-product solutions suitable for use in the process of this invention are described in U.S. Pat. Nos. 3,668,204; 3,712,891; 3,835,134; and 3,835,135 where cyanuric acid or an alkali metal cyanurate is reacted with hypochlorous acid or a mixture of chlorine and sodium hypochlorite to produce di- and/or trichloroisocyanuric acid. Aqueous solutions containing salts of polychloroisocyanuric are also suitably used in the process of this invention and include, for example, those obtained in the processes described in U.S. Pat. Nos. 3,035,056; 3,072,654; 3,157,649; 3,270,017 and 3,501,468.

Also suitable are solutions of off-specification chloroisocyanurate products or "floor sweepings" which can be diluted with water, filtered, if necessary, and the solutions fed to the recovery process.

In the improved process of the present invention, an aqueous solution of a chloroisocyanuric acid compound of the type described above is acidified to convert the chloroisocyanurate compound into cyanuric acid and chlorine.

Any acid having an ionization constant larger than that of isocyanuric acid can be employed. However, it is preferred to use a mineral acid such as hydrochloric acid, sulfuric acid, phosphoric acid or nitric acid. A sufficient amount of mineral acid is added to react with substantially all chlorine chemically combined in the chloroisocyanuric acid compound present in the aqueous solution. In general, the ratio of hydrogen atoms provided by the mineral acid to chlorine atoms in the chloroisocyanuric acid compound ranges from about 1:1 to about 2:1, and preferably from about 1:1 to about 1.5:1. For example, when using a monovalent acid such as hydrochloric acid, the stoichiometric amount of acid required to release all chlorine from trichloroisocyanuric acid is a molar ratio of hydrochloric acid to trichloroisocyanuric acid of 3:1 and the stoichiometric amount of hydrochloric acid required to release chlorine from dichlorocyanuric acid is a molar ratio of hydrochloric acid to dichloroisocyanuric acid of 2:1. Similarly, using a divalent acid such as sulfuric acid, the stoichiometric amount is a molar ratio of $H_2SO_4$ to trichloroisocyanuric acid of 1.5:1 and the stoichiometric amount is a molar ratio of $H_2SO_4$ to dichloroisocyanuric acid of 1:1. Equivalent proportions of trivalent acids such as phosphoric acid are employed. In order to assure complete removal of the chlorine, it is preferred to use an excess of mineral acid above the stoichiometric amount required for the specific type of chloroisocyanuric acid compound present in the aqueous solution. This excess should be, however, a moderate amount to minimize the expense of the reagents used in treating the chloroisocyanuric acid compound solution, and where required, the subsequent neutralization of the acidified chlorinedepleted cyanuric acid recovered. In the process of the present invention, it is preferred to use hydrochloric acid for chlorine release in the stripping column, as it introduces no new anionic group into the solution being reacted which must later be discarded or recovered. In order to simplify the disclosure of the invention, it will be described hereinafter in terms of hydrochloric acid. When using hydrochloric acid to release chlorine from an aqueous solution containing a chloroisocyanuric acid, any suitable amount of acid can be used. For example, where the chloroisocyanuric acid compound is trichloroisocyanuric acid, a molar ratio of HCl to trichloroisocyanuric acid in the range of about 3:1 to about 4.5:1 is suitable. When dichloroisocyanuric acid solutions are treated, a molar ratio of HCl to dichloroisocyanuric acid in the range of about 2:1 to about 3:1 is maintained. Preferably, an excess of hydrochloric acid to the chloroisocyanuric acid compound is in the range from about 10 to about 30 percent.

The reactions which take place during the acidification process, using for example, an aqueous solution of trichloroisocyanuric acid and hydrochloric acid are believed to be represented by the following equations:

$$Cl_3CA + 3H_2O \rightleftarrows 3HOCl + 3CA$$

$$HOCl + HCl \rightleftarrows Cl_2(aq) + H_2O$$

$$Cl_2(aq) \rightleftarrows Cl_2(g),$$

where CA represents cyanuric acid.

During the acidification and stripping process, it is important to maintain the temperature of the aqueous solution high enough so that the cyanuric acid formed will remain dissolved in the aqueous solution and not be deposited as a scale on reactor surfaces, column packing and other components used in the separation process. The temperature selected will depend on the concentration of the chloroisocyanuric acid in the solution and the pressure employed.

While any concentration of chloroisocyanuric acid compound may be treated by the novel process of the present invention, it is preferable to maintain the concentration of the chloroisocyanuric acid compound in the aqueous solution at about 4 percent or less by weight when these operations are run at substantially atmospheric pressure. Solutions having concentrations of cyanuric acid greater than this can be diluted by the addition of water or by adjusting the concentration of the mineral acid solution.

In one embodiment, the aqueous solution is heated in heater 12 prior to acidification to a temperature sufficiently high enough to assure the cyanuric acid formed remains dissolved in the aqueous solution. Where the acidification or stripping is conducted at atmospheric pressure, suitable temperatures are those in the range of from about 15° to about 100° C., and preferably at from about 25° to about 50° C.

In another embodiment, the reactor or stripping column in which the acidification and/or stripping takes place is heated to maintain the solution at the temperature described above.

While the acidification and stripping are normally conducted at substantially atmospheric pressure, these operations can be carried out at sub-atmospheric pressures or super-atmospheric pressures, if desired.

Following acidification, the acidified reaction mixture containing dissolved cyanuric acid and dissolved chlorine is introduced into a stripping column, for example, at the upper end of a stripping column. A gas inert to the components of the reaction mixture is fed, for example, countercurrently up through the mixture to strip chlorine gas from the solution.

To prevent cyanuric acid from depositing on column surfaces, packing materials and from plugging openings in the gas inlet device, it is preferred to heat the inert gas prior to its introduction into the column. The heated gas may be at any suitable temperature which does not boil the solution in the stripping column or thermally decompose the cyanuric acid. Suitable temperatures for the heated gas include, for example, those above about 35° C.

Any gas inert to the reaction mixture can be used in stripping chlorine, for example, air, nitrogen, carbon dioxide, steam or mixtures thereof.

Preferred embodiments of the inert gas include a mixture of steam and air or a mixture of steam and nitrogen. In addition to maintaining the temperature of the reaction mixture within the desired ranges, humidifying the inert gas with steam prevents evaporation and subsequent evaporative cooling of the aqueous solution during stripping.

In the conventional operation of a stripping column such as a packed column, the inert gas is fed to the column, countercurrent to the liquid, in sufficient amounts so that the gas phase is continuous within the packing area and the liquid flow is such that the liquid phase is non-continuous. During stripping, a thin layer of liquid flows over the packing such that liquid drips between non-contiguous pieces of packing. Liquid occupies a very small portion of the voids in the packing and the packing is not submerged in liquid. In stripping $Cl_2$ from acidified aqueous solutions containing cyanuric acid, this conventional method of operation results in a large volume of stripping gas which must be treated, for example, in a scrubber, to recover the volume of chlorine present. In addition, this procedure requires a larger stripping column to effectively reduce the chlorine concentration of the stripped solution to the desired amounts while also requiring a larger inert gas feeding system and a larger gas heater. All of these requirements add to the cost of recovering the desired chlorine and cyanuric acid values.

Surprisingly, it has been found that effective stripping could be accomplished using smaller sized equipment and reduced amounts of the inert gas by conducting the stripping operation while maintaining the stripping column partially or completely full of liquid to provide a continuous liquid phase. Thus in this unconventional method of the present invention, the liquid is the continuous phase and the inert gas is the noncontinuous phase. This novel method operates, for example, when using a packed column, so that the packing is submerged to a significant extent in the liquid. The inert gas bubbles up through the liquid with the packing serving to disperse or break up the inert gas bubbles. Liquid occupies a substantial portion of the packing-free spaces or voids and the column is operated at liquid levels of from about 10 to about 100, and preferably from about 70 to about 100 percent of the total height of the stripping column.

The desired liquid levels can be maintained with any suitable level control device, for example, one which controls the rate of removal of the dechlorinated aqueous solution containing cyanuric acid from the stripping column in relation to the liquid level in the column.

During the stripping operation, the acidified aqueous solution is fed to the stripping column at a rate which maintains the weight ratio of the liquid feed rate to the gas feed rate in the range of from about 5:1 to about 50:1, and preferably from about 10:1 to about 20:1.

In addition to providing effective chlorine stripping, use of the method of the present invention results in a short retention period for the aqueous solution of cyanuric acid. A suitable retention time for the solution in the stripping column is that from about 0.5 to about 10, preferably from about 1 to about 6, and more preferably from about 1 to about 3 minutes.

When employing a packed column as the stripping reactor, any packing material which has suitable voids or free spaces may be used including, for example, rings, saddles, grid packings, tellerettes, etc.

In addition to a packed column, any suitable stripping column may be used including sieve plate columns, tray columns or disk- and doughnut columns.

Stripping removes substantially all of the chlorine from the aqueous solution. The solution leaving the bottom of the stripping column has a concentration of available chlorine of less than about 100 parts per million, and preferably from about 0 to about 20 parts per million.

To recover cyanuric acid values, the chlorinedepleted aqueous solution is introduced to a reactor where it is neutralized by the addition of a base such as an alkali metal hydroxide or an alkali metal carbonate. Suitable bases include sodium hydroxide, potassium hydroxide, lithium hydroxide, sodium carbonate, potassium carbonate and lithium carbonate, with sodium hydroxide or sodium carbonate being preferred. Sufficient base is added to provide the chlorine-depleted aqueous solution with a pH in the range of from about 4.0 to about 11.0, depending on the product to be recovered. For cyanuric acid recovery, a pH in the range of about 4.0 to about 6.0, and preferably from about 4.5 to about 5.5 is quite satisfactory.

If desired, the chlorine-depleted aqueous solution may be treated with sufficient base to raise the pH of the solution to the range of about 7.0 to about 11.0, and preferably from about 8.0 to about 9.0 and an alkali metal cyanurate formed. This permits increased recovery of the cyanuric acid values where the monoalkali metal cyanurate is formed because of its lower solubility.

Before, during or after neutralization it may be desirable to cool the solution to a temperature of from about 0° to about 30° C. to precipitate the cyanuric acid or alkali metal cyanurate produced. When cooling of the solution takes place, agitation, and/or circulation of the solution is desirable to keep the cyanuric acid precipitate suspended in the solution and prevent it from coating the neutralizing reactor.

Recovery of the cyanuric acid can be accomplished in a filter such as a bag filter or rotary filter or a centrifuge.

An alkali metal cyanurate can be recovered in a centrifuge or a thickening device or process so that the amount of moisture in the recovered product can be controlled.

The following examples are presented to further illustrate the invention without any intention of being limited thereby. All parts and percentages are by weight unless otherwise specified.

EXAMPLE 1

An aqueous slurry of trichloroisocyanuric acid was prepared by a process in which an aqueous slurry of monosodium cyanurate was reacted with hypochlorous acid and chlorine gas. After filtration and recovery of the product, a filtrate containing 0.8 percent of trichloroisocyanuric acid and 6.5 percent of sodium chloride was heated in a heat exchanger to a temperature of 35° C. Following heating, the aqueous solution was pumped to a reaction vessel. Hydrochloric acid (32 percent) was introduced and the aqueous solution acidified. In the reaction vessel, some chlorine gas was released and this gas was piped to a scrubber containing a solution of sodium hydroxide to produce a solution of sodium hypochlorite. The acidified solution containing dissolved cyanuric acid, dissolved chlorine, hypochlorous acid, and sodium chloride was fed to a 10-ft. stripping column packed with ceramic intalox saddles. After the acidified solution reached a level of about 4 feet, air heated to a temperature of 50° C., was fed through an air sparge at the lower end of the column at a rate to provide a ratio of liquid to gas of 15:1. During continuous stripping of the acidified solution of trichloroisocyanuric acid, aerated liquid occupied about 100 percent of the height of the stripping column. The liquid level in the column was controlled by limiting the rate of flow of the chlorine-stripped solution of cyanuric acid from the bottom of the column. Air containing chlorine was removed from the top of the column and fed to the scrubber. The chlorine-stripped solution removed from the bottom of the columm had an available chlorine concentration of 20 parts per million and its temperature was 35° C. This recovered solution containing dissolved cyanuric acid was transferred from the column to a jacketed reactor where its pH was adjusted to 4.4±0.5 by the addition of a solution of sodium hydroxide. Ethylene glycol solution, at a temperature of −5° C., was circulated through the jacket of the reactor to cool the cyanuric acid solution to 10° C. During cooling, the solution was agitated and recirculated to keep cyanuric acid suspended in the solution. The cooled solution was pumped through a 150 micron bag filter to separate the cyanuric acid crystals from the solution. During the chlorine stripping and cyanuric acid recovery, this procedure prevented the scaling of packing materials and equipment internals by precipitated cyanuric acid.

COMPARATIVE EXAMPLE A

The filtrate of the same composition and temperature as that of Example 1 was acidified by the procedure of Example 1. The acidified solution and air was fed to the 10-ft. stripping column used in Example 1 at the same liquid to gas ratio. The stripping column was operated in the conventional manner where the liquid was not retained in the packed section of the tower to provide a liquid level. The aqueous solution removed from the bottom of the column had an available concentration in the range of 300 to 1000 parts per million, indicating that inefficient and inadequate stripping of the dissolved chlorine had taken place.

Using the novel process of the present invention, as illustrated in Example 1, results in effective chlorine stripping, where the available chlorine concentration of the stripped solution is reduced to about 20 parts per million. However, the conventional operation of the stripping column, as shown in Comparative Example A, is inadequate and results in stripped solutions containing excessive amounts of available chlorine (300-1000 ppm).

COMPARATIVE EXAMPLE B

The procedure of Example 1 was duplicated exactly in the apparatus of Example 1 with the exceptions that the acidified solution was fed to the stripping column at a temperature of 15° C. and the air supplied to the stripping column was not heated. Effective chlorine removal was accomplished, but the cyanuric acid precipitated and adhered to and scaled the column internals so badly that in a short time the fresh acidified solution fed to the column was unable to flow through the column. Stripping had to be discontinued and the column cleansed.

Example 1 thus illustrates the necessity of heating the acidified solution to a temperature which retains cyanuric acid in solution to avoid the precipitation of cyanuric acid and the scaling of equipment which resulted in Comparative Example B.

EXAMPLES 2-7

Demineralized water (593 pounds) and 50 pounds of NaCl were charged to a reactor having an agitator and heated to 50° C. To this solution was added 5.2 pounds of trichloroisocyanuric acid (TCCA) and the mixture agitated to form a solution of trichloroisocyanuric acid in the aqueous saline solution. Sufficient 32 percent HCl was added to the reactor to provide a molar ratio of HCl to TCCA of about 3.6:1, representing an excess of HCl of 21 percent. The acidified solution had an available chlorine concentration in the range of from about 1300 to about 1550 parts per million. The acidified solution was continuously fed to the top of the stripping column packed with ceramic intalox saddles. The solution feed rate was held constant at 2210 pounds per hour per square foot. Air was heated in a heat exchanger to a temperature of 50° C., and fed to the bottom of the column. Heated air percolated up through the column countercurrent to the flow of the acidified solution. The liquid level in the column was maintained at a height of 10 feet by a level control which regulated the rate of liquid exiting the column bottom. The air flow rate was varied periodically. For each air flow rate employed, the liquid level in the column and the residence time for the solution was determined and the available chlorine concentration of the chlorine-depleted acidified solution determined. The results are presented in Table I below. In all of the examples, the ratio of the feed rate of liquid to that of inert gas was low enough and temperature of the acidified solution was high enough to effectively remove chlorine from the solution while preventing precipitation of cyanuric acid on the column surfaces and packing material. The heated air prevented cyanuric acid from precipitating and plugging the air distributor.

TABLE I

| Example No. | Feed rate of acidified solution (L) in lbs./hr./sq. ft. | Feed rate of heated air (G) in lbs./hr./sq. ft. | Ratio of L to G | Solution Residence Time in Minutes | Available chlorine in Effluent in ppm |
|---|---|---|---|---|---|
| 2 | 2210 | 46 | 48 | 4.6 | 69 |
| 3 | 2210 | 97 | 23 | 4.3 | 18 |
| 4 | 2210 | 143 | 15 | 4.1 | 14 |
| 5 | 2210 | 46 | 48 | 6.4 | 52 |
| 6 | 2210 | 97 | 23 | 5.9 | 11 |
| 7 | 2210 | 143 | 15 | 5.7 | 9 |

COMPARATIVE EXAMPLE C

Using the procedure of Examples 2–7, a solution containing 0.8 percent trichloroisocyanuric acid and 7 percent sodium chloride was fed to a heat exchanger which heated the solution to about 50° C. The solution was acidified with concentrated hydrochloric acid using a molar ratio of HCl to trichloroisocyanuric acid of 3.75:1, an acid excess of 25 percent. The acidified solution was fed to the top of the stripping column. Dry air, at a temperature of 25° C., was fed to the bottom of the column through a sparge pipe. The ratio of the feed rate of the solution to the feed rate of the air was maintained between 10 and 20. Within a short period after the stripping operation began, air flow through the sparge pipe was reduced and was finally restricted all together. Examination of the pipe showed the sparge holes had been plugged with deposits of cyanuric acid.

The process of Examples 2–7 heated the air prior to feeding it to the stripping column. This practice eliminates the problems caused when air at ambient temperatures is used.

What is claimed is:

1. In a process for recovering chlorine values from an aqueous solution of a chloroisocyanuric acid compound selected from the group consisting of polychloroisocyanuric acids, alkali metal salts of polychloroisocyanuric acid and mixtures thereof by reacting a mineral acid with said aqueous solution of said chloroisocyanuric acid compound to produce a reaction mixture containing dissolved chlorine and cyanuric acid in an aqueous solution, feeding said aqueous solution to a stripping column and removing said chlorine from said reaction mixture with an inert gas, and recovering said gaseous chlorine, the improvement which comprises maintaining a continuous liquid phase and a non-continuous gas phase in said stripping column.

2. The process of claim 1 in which the aqueous solution in said stripping column is maintained at a level of from 10 to about 100 percent of the height of said stripping column.

3. The process of claim 2 in which said stripping column is selected from the group consisting of packed columns, sieve plate columns, tray columns, and disk- and doughnut columns.

4. The process of claim 1 in which said inert gas is selected from the group consisting of air, nitrogen, carbon dioxide, steam or mixtures thereof.

5. The process of claim 2 in which said stripping column is maintained at a temperature high enough to dissolve cyanuric acid formed in said aqueous solution.

6. The process of claim 5 in which said stripping column is a packed column maintained at substantially atmospheric pressure.

7. The process of claim 6 in which said inert gas is fed to said stripping column countercurrent to said aqueous solution, and said gas is at a temperature above about 35° C.

8. The process of claim 7 in which the weight ratio of the flow rate of aqueous solution to the flow rate of said inert gas in said stripping column is from about 5:1 to about 50:1.

9. The process of claim 7 in which said reaction mixture is retained in said stripping column for a period of from about 0.5 to about 10 minutes.

10. The process of claim 7 in which said gaseous chlorine removal from said stripping column is fed to a scrubber containing an aqueous solution of a base.

11. The process of claim 7 in which said mineral acid is hydrochloric acid.

12. The process of claim 7 in which said chloroisocyanuric acid compound is trichloroisocyanuric acid.

13. The process of claim 7 in which said aqueous solution removed from said stripping column has an available chlorine content of less than about 100 parts per million.

14. The process of claim 7 in which said inert gas is selected from the group consisting of a mixture of steam and air and a mixture of steam and nitrogen.

15. The process of claim 7 in which said reaction mixture in said stripping column is maintained at a temperature of from about 35° to about 100° C.

16. The process of claim 7 in which said level of said reaction mixture in said stripping column is maintained at from about 70 to about 100 percent of the height of said stripping column.

17. The process of claim 16 in which said weight ratio of said flow rate of aqueous solution to said flow rate of said inert gas in said stripping column is from about 15:1 to about 25:1.

18. A process for recovering chlorine values from an aqueous solution of a chloroisocyanuric acid compound selected from the group consisting of polychloroisocyanuric acids, alkali metal salts of polychloroisocyanuric acids, and mixtures thereof, which comprises:
    (a) heating said aqueous solution,
    (b) acidifying said aqueous solution with a mineral acid to form a reaction mixture comprising gaseous chlorine and cyanuric acid,
    (c) feeding said reaction mixture to a stripping column,
    (d) heating a gas inert to said reaction mixture,
    (e) passing said inert gas through said reaction mixture to remove said gaseous chlorine from said reaction mixture to a chlorine recovery vessel, and
    (f) maintaining the level of said reaction mixture in said stripping column at from about 70 to about 100 percent of the height of said stripping column.

19. The process of claim 18 in which a chlorine-depleted aqueous solution of cyanuric acid is removed from said stripping column, cooled to a temperature of from about 0 to about 35° C., and treated with an alkaline compound selected from the group consisting of alkali metal hydroxides and alkali metal carbonates to provide said solution with a pH of from about 4 to about 11.

20. The process of claim 19 in which said alkaline compound is an alkali metal hydroxide.

21. The process of claim 19 in which the pH is from about 4.0 to about 6.0 and cyanuric acid is recovered from said chlorine-depleted solution.

22. The process of claim 19 in which said pH is from about 7.0 to about 11.0 and an alkali metal cyanurate is recovered from said chlorine-depleted solution.

* * * * *